United States Patent
Tiemens et al.

(10) Patent No.: US 7,210,484 B1
(45) Date of Patent: May 1, 2007

(54) BAFFLED EARPLUG

(75) Inventors: Jim Tiemens, Laguna Nigel, CA (US);
David Mulvey, San Diego, CA (US);
Raul Cortez, Chula Vista, CA (US)

(73) Assignee: Howard Leight Industries, LLC, San Diego, CA (US)

( * ) Notice: Subject to any disclaimer, the term of this patent is extended or adjusted under 35 U.S.C. 154(b) by 0 days.

(21) Appl. No.: 11/367,684

(22) Filed: Mar. 3, 2006

(51) Int. Cl.
*A61F 11/00* (2006.01)
*A61F 11/06* (2006.01)

(52) U.S. Cl. ............. 128/864; 128/865; 128/867
(58) Field of Classification Search ........... 128/864, 128/867, 865
See application file for complete search history.

(56) References Cited

U.S. PATENT DOCUMENTS 4,060,080 A * 11/1977 Akiyama ............... 128/865
4,384,575 A    5/1983 Asker
4,434,794 A    3/1984 Leight
5,957,136 A    9/1999 Magidson et al.
6,761,173 B1 * 7/2004 Kuno et al. ............ 128/864

\* cited by examiner

*Primary Examiner*—Justine R. Yu
*Assistant Examiner*—K C Matter
(74) *Attorney, Agent, or Firm*—Leon D. Rosen

(57) ABSTRACT

An earplug (10) with a body front portion (22) for insertion into a person's ear canal, has a pocket (30) to increase comfort and is constructed to enhance noise attenuation. The pocket, which allows easier compression of the body front portion for increased comfort, has a plurality of baffles (50) that attenuate sound better than a pocket without baffles. The pocket with baffles is formed by a core pin (80) that lies in an injection mold (82) and that forms the pocket, the core pin having a plurality of slots (81) that form the baffles. The pocket includes a rear portion (36) that forms a wide passage, and the earplug includes a blocker portion (90) that partially or completely closes off the rear pocket passage.

8 Claims, 4 Drawing Sheets

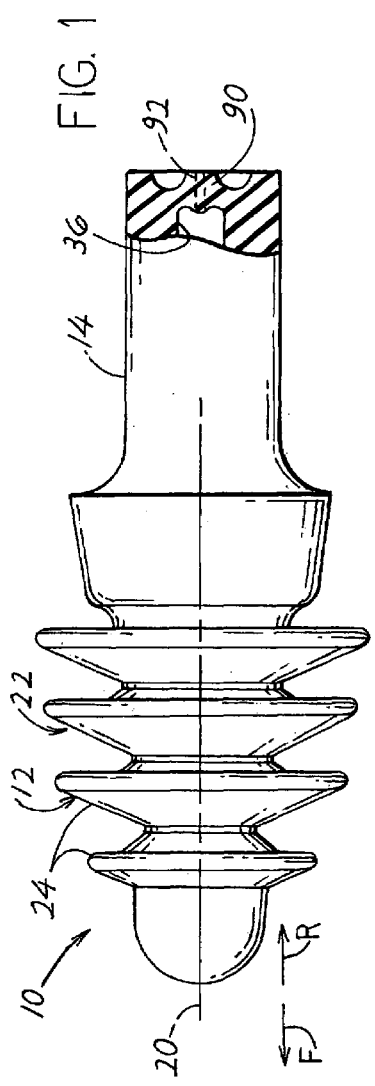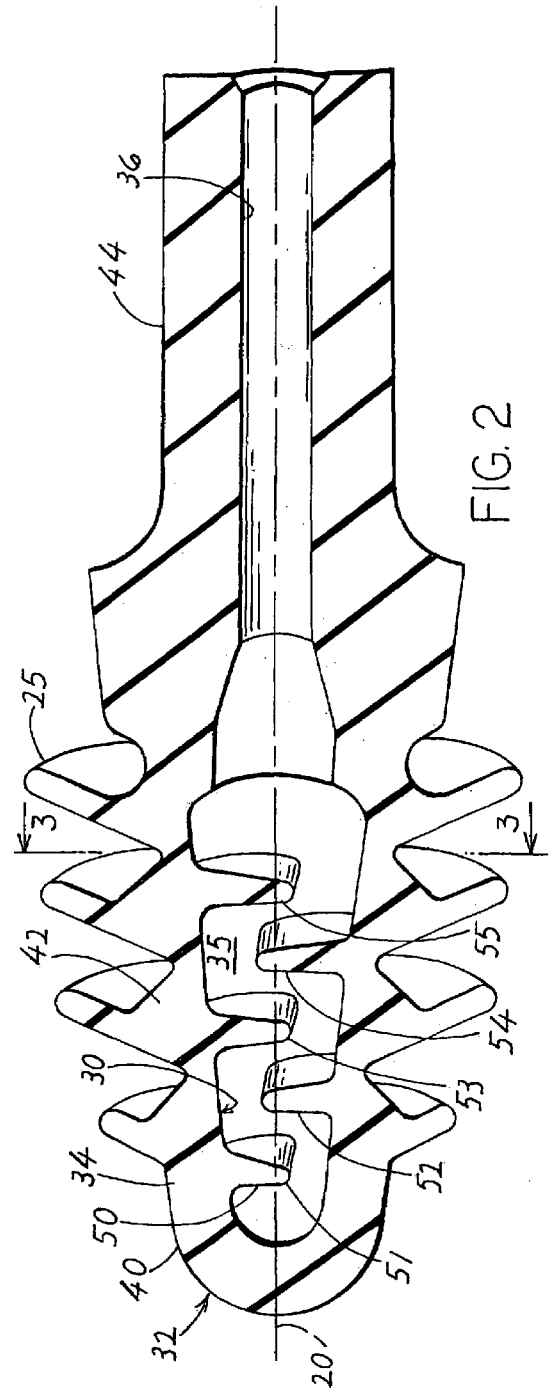

BAFFLED EARPLUG

BACKGROUND OF THE INVENTION

One type of earplug is formed primarily of elastomeric material and has a pocket containing gas (air) that enables the earplug to be more easily compressed during insertion and to remain compressed in the ear. This enables easier insertion into a person's ear canal and reduces pressure on the walls of the ear canal to increase comfort. A method for forming an earplug with a desired molded outside shape such as with flanges, and with an internal pocket structure with enhanced noise attenuation characteristics would be of value.

SUMMARY OF THE INVENTION

In accordance with one embodiment of the invention, an earplug is provided that can be constructed with a molded outer surface and with an internal pocket, wherein the earplug has enhanced noise blocking, or attenuating, characteristics and still can be constructed at low cost. The earplug body is formed with a pocket and with a plurality of internal fins or baffles that break up the otherwise smooth walls of the pocket. The baffles are spaced along the axis of the earplug. The baffles each blocks at least about half of the cross section of the pocket as seen when looking along the earplug axis. Alternate baffles project from opposite sides of the pocket and partially across the pocket. When the earplug is compressed in the ear, the baffles each can block almost the entire cross section of the pocket.

The earplug is formed by placing a core pin in a mold that forms the outside surface of the earplug, to form an earplug in the cavity that exists between the mold and the core pin. The core pin, which is elongated along the axis of the earplug, has a plurality of slots spaced along the axis, with molding material filling the slots during injection molding to form the baffles. Core pin slots that are progressively spaced along the axis, lie on opposite sides of the core pin axis to leave baffles that project into the pocket from alternate sides of the pocket. Applicant finds that due to the elasticity of the injection molded material, the core pin with baffle-forming slots can be pulled out of the rear of the earplug after the molding operation. The rear of the pocket is then partially or fully sealed against the free passage of sound therein.

The novel features of the invention are set forth with particularity in the appended claims. The invention will be best understood from the following description when read in conjunction with the accompanying drawings.

BRIEF DESCRIPTION OF THE DRAWINGS

FIG. 1 is a side elevation view of an earplug of the present invention, showing an earplug body and showing a means for blocking the free passage of sound into the rear end of the earplug body.

FIG. 2 is a sectional and isometric view of the earplug body of FIG. 1, before the pocket rear portion is blocked.

DESCRIPTION OF THE PREFERRED EMBODIMENTS

Figure 3:
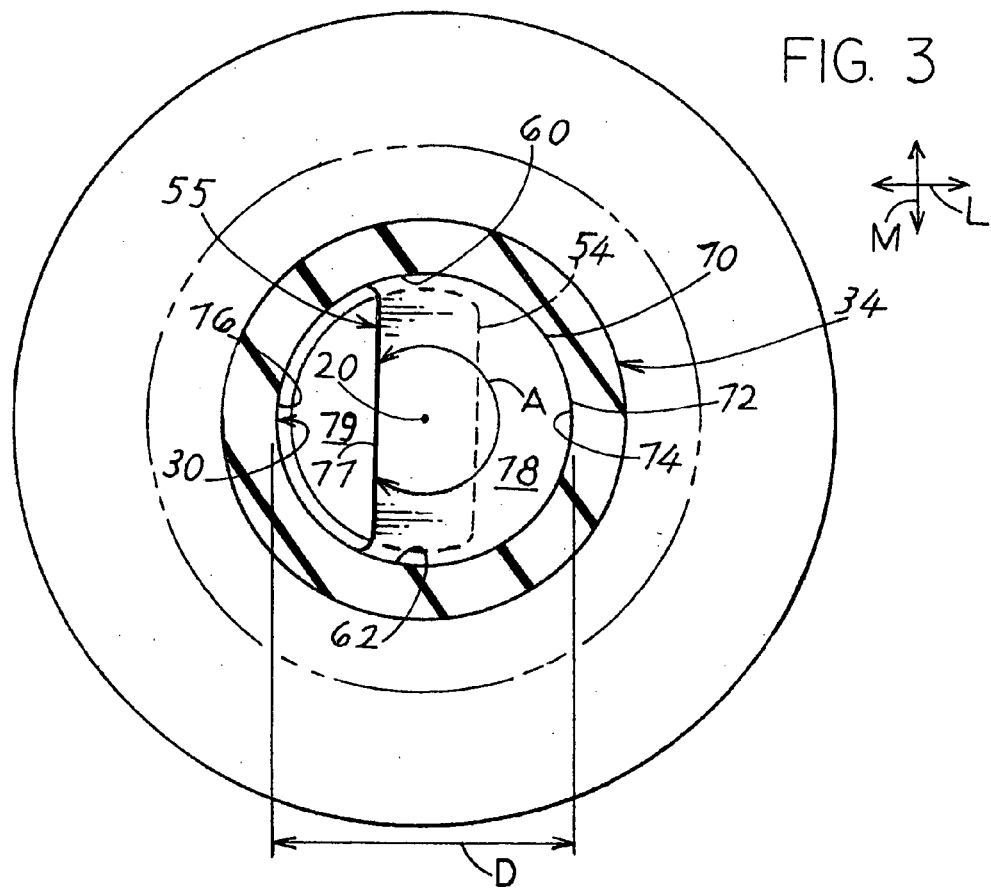
FIG. 3 is a sectional view taken on line 3—3 of FIG. 2.

FIG. 1 illustrates an earplug 10 having an earplug body 12 with a stem 14. The earplug has an axis 20 that extends in front and rear directions F, R. A front portion 22 of the body is inserted into a person's ear canal by holding the stem and pushing it forward into the ear canal. Flanges 24 on the outside of the body are deflected rearwardly and radially inwardly as the earplug is inserted, and seal against the walls of the ear canal. As shown in FIG. 2, the earplug body has a pocket 30 that is formed within a shell 32 of the earplug. The pocket allows the shell walls to be easily compressed radially inward (towards the axis 20) as the earplug is inserted into a person's ear canal, to facilitate such insertion and to provide greater comfort to the person. The pocket has a front portion 35 that lies within the front portion of the body, and the pocket has a rear that forms a passage or pocket rear portion 36.

The shell 32 has a largely sleeve portion or sleeve 34 with a front end 40, side walls 42, and a rear portion 44. The shell forms a plurality of baffles 50 that each extends from the inside of the sleeve and at least partially across the pocket, with five baffles 51–55 being present in the earplug illustrated in FIG. 2. The baffles serve to more completely block sound from passing forwardly through the earplug. Each baffle projects primarily perpendicular to the axis 12 and at least partially across the pocket. FIG. 3, which is taken on line 3—3 of FIG. 2, shows that the baffle 55 extends from one lateral L side 74 of the pocket 30 towards the laterally opposite side 76. The baffle has a merging portion 70 where the baffle merges with the sleeve 34 of the earplug, along an angle A. The merging portion has a middle 72 at pocket side 74. The baffle has a free edge 77 lying opposite the middle 72 of the merging portion, with the free edge extending across most of the diameter D of the pocket between longitudinally M opposite side portions 60, 62 at the location of the baffle. FIG. 3 also shows that the baffle 55 forms a sound blocking portion 78 that extends across and covers at least about half (at least 45%) of the cross-sectional area of the pocket immediately forward and rearward of the baffle and preferably covers more than half of the pocket cross sectional area as seen in a view taken along the axis 12. The blocking portions of all the baffles block an average of at least half of the pocket cross-sections.

Figure 4:
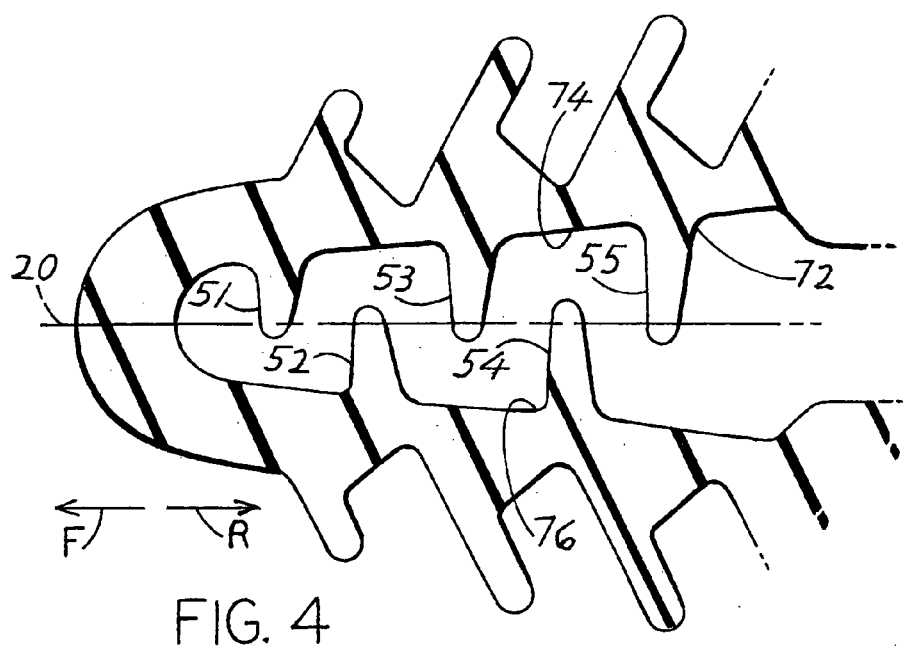
FIG. 4 is a sectional view of a front portion of the earplug body of FIG. 4

FIG. 4 shows that the baffles 51–55 each extends from the middle such as 72 of its merging portion to at least the axis 20 of the earplug, and preferably beyond the axis. Also, the baffles are staggered, with the blocking portions of adjacent baffles blocking opposite sides of the pocket cross section. Thus, baffle 54 blocks a portion of the pocket extending from pocket side 76 towards the opposite pocket side 74 while adjacent baffles 53 and 55 each blocks portions of the pocket that extend from the opposite side 74 of the pocket.

Figure 7:
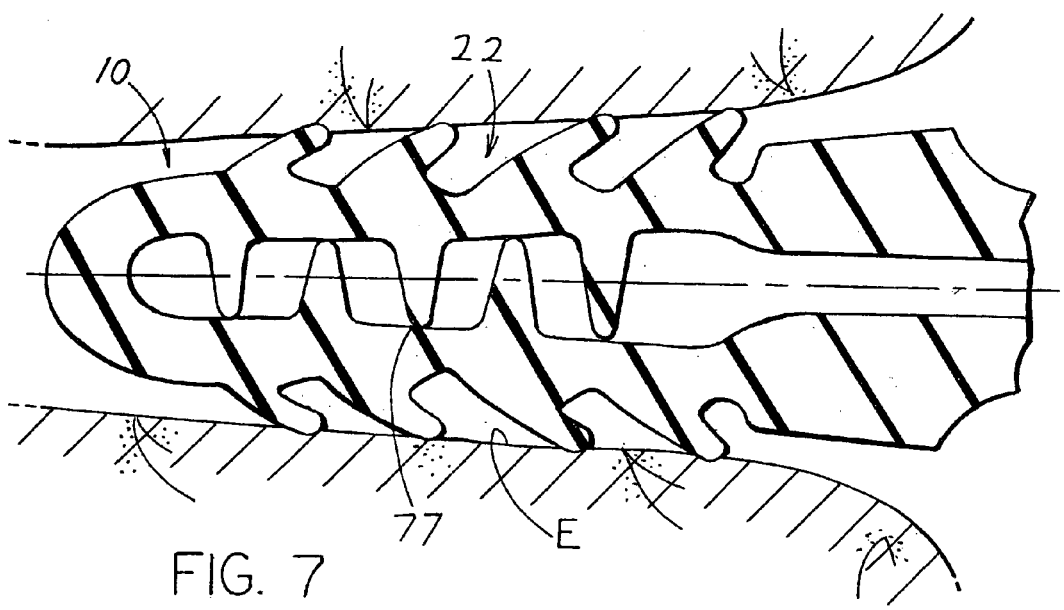
FIG. 7 is a sectional view similar to FIG. 4, but with the earplug front portion lying compressed in a person's ear canal.

FIG. 7 illustrates the behavior or the baffles when the earplug is inserted into an ear canal E of average diameter (0.3 inch). As the plug front portion 12 is compressed, the free edge 77 of some of the baffles may contact the opposite wall, forming a separate partially sealed chamber. Any sound energy passing through the center of the earplug meets a series of absorption barriers and results in a net attenuation improvement. At the same time the intermeshed baffles maintain flexibility to adapt to the complex ear canal size, shape, and curvature, and sufficient stiffness is preserved for easy insertion without columnar collapse.

The baffles block more sound than is blocked by an earplug of the same size, shape and construction but wherein there are no baffles in the pocket. The pocket 30 is filled with air that has a much lower density than the density of the elastomeric material of the baffles 50. As a result, sound passing forwardly into the pocket encounters many interfaces between the higher density elastomeric material and the air in the pocket, and some of the sound is reflected at those interfaces. The reflected sound passes further though the air and elastomeric material before reaching the front end of the earplug and passing into the ear canal, and more of the sound is absorbed than sound that passes straight though a pocket without baffles.

Figure 5:
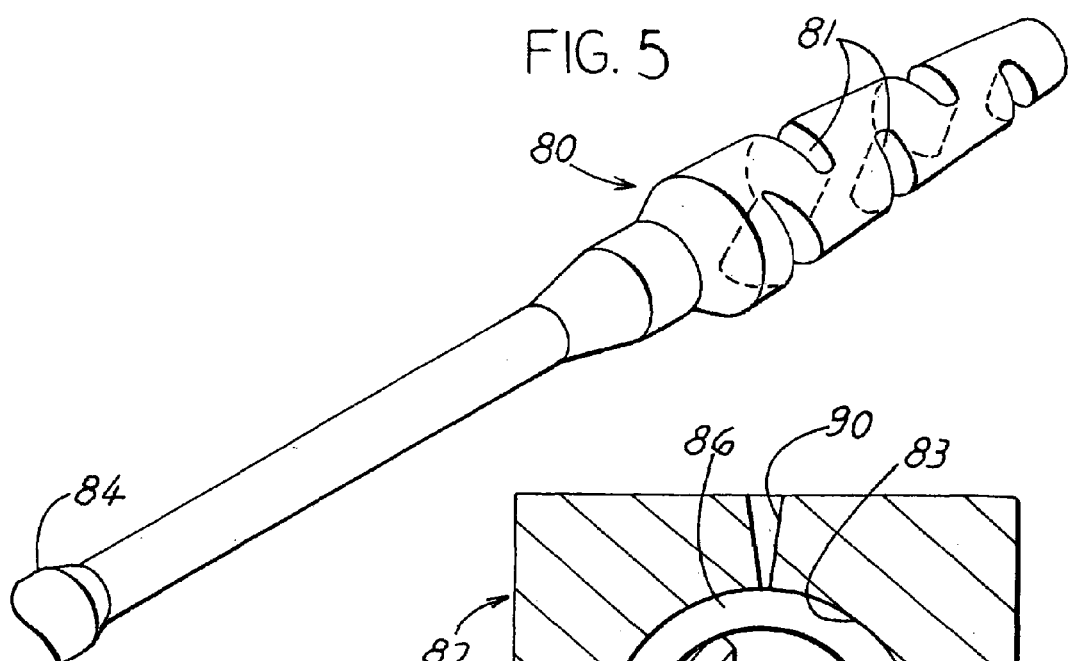
FIG. 5 is a partial isometric view of the core pin used in the construction of the earplug of FIG. 1.
Figure 6:
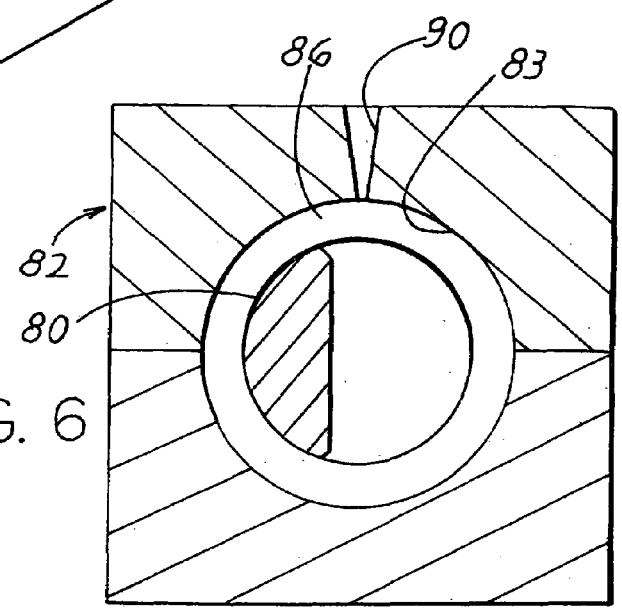
FIG. 6 is a sectional view showing the molding process of the invention.

The earplug is manufactured by the use of a core pin of the construction shown at 80 in FIG. 5 that has slots 81 that will form the baffles. The earplug is formed in a mold shown at 82 in FIG. 6, which has a mold space 83. The core pin rear end 84 is fixed in position and the rest of the core pin is cantilevered. The core pin and walls of the mold form a cavity 86 between them. Flowable elastomeric material is flowed into the mold through a sprue hole and gate 90 in the mold. Some suitable elastomeric materials to achieve the combination of characteristics for this earplug are silicone rubbers and a variety of thermoplastic elastomers including TPE, PVC, TPU and TPR. An elastomeric material is a material with a Young's modulus of elasticity of no more than 50,000 psi. The most suitable materials are elastomers, which are heated to make them flowable and that then cool so they become solid but still flexible.

After the earplug body has been molded and the earplug body material has solidified, the mold is opened so the earplug can expand. Then, the core pin is pulled rearwardly out of the earplug. Applicant finds that a core pin of the shape illustrated can be pulled out of the earplug, even through the small stem passageway, and will leave the baffle structured pocket behind.

After the earplug body shown in FIG. 2 has been molded, the rear portion 36 of the pocket which forms a passage for withdrawal of the core pin, must be partially or fully blocked to prevent the free inflow of sound (the passage of sufficient sound to appreciably decrease the noise-blocking ability of the earplug, such as at least one dB or one-half dB). When the earplug of FIG. 1 is designed to not be tied to another earplug by a cord, blocker portion 90 is provided to block all or almost all of the pocket rear portion 36. It is possible to provide a hole 92 of small cross-section to allow air to escape and flow back in, but this is not necessary.

A small hole, or pin hole can be left in the rear portion of the passage, to allow air to escape when the earplug is compressed in the ear canal, and to allow air to return to the pocket when the earplug is removed. Such pin hole preferably has a diameter of no more than 0.5 mm and has a cross-sectional area no more than 0.25 square millimeters in order to prevent significant sound from entering the pocket. However, applicant finds that the rear portion of the passage can be completely sealed, and the earplug still can be readily inserted into the ear canal, although a pin hole helps in such insertion.

In the earplug illustrated in FIGS. 1 and 2 that applicant has manufactured and successfully tested, the earplug largest flange 25 had a diameter of 11.8 millimeters and most of the passage rear portion 36 had a diameter of 1.5 mm. The baffles were axially spaced (center-to-center) by 1.5 mm (preferably 1.0 to 2.0 mm). The blocker portion 94 was formed by heat staking the earplug stem to prevent the forward free flow of sound into the pocket. The pocket 30 has a volume of about 50 $mm^3$ which is reduced when the earplug is compressed during insertion into the ear canal.

Applicant has constructed fifteen core pins of slightly different designs, to produce fifteen variations of the earplug illustrated in FIGS. 1–6. Applicant found that the design of FIGS. 1–6 resulted in high sound blockage and a core pin that could be readily removed from the earplug after molding and that did not break at one of its slots. Depending on the exact structure of the internal baffles, the low-medium and high frequency attenuation effectiveness of the earplug can be adjusted. A very flat attenuation performance was achieved with the construction of FIGS. 2–6. At a range of frequencies, the noise reduction improved by 2 to 5 dB over the same earplug with a pocket of the same shape and size but without baffles.

Figure 8:
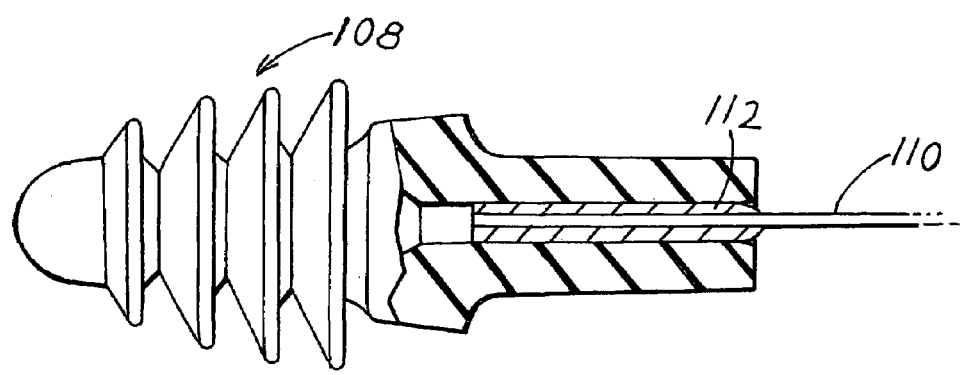
FIG. 8 is a partially sectional view of an earplug wherein the rear of the pocket is blocked by a ferrule that holds an end of a cord.

FIG. 8 illustrates an earplug 108 with a sound blocker portion formed by a cord 110 which lies in a ferrule 112, and with the ferrule lying in and blocking all or most of the pocket rear portion. The cord ties together two earplugs of the same construction. The cord can be bonded by a crimp or adhesive to the ferrule and the ferrule is bonded by adhesive to the walls of the passage of the pocket rear portion.

The number, thickness, tapers, lengths and angles of orientations of the baffles can be varied to assure comfort for the person who uses the earplug while providing maximum sound blocking especially at the frequencies of most interest. Although applicant prefers to use an air filed pocket, it is possible to fill the pocket with a very soft foam, a filter element, gel or matt of fibers, or other suitable soft material. It also would be possible to mold the earplug with a pocket but no baffles, and then insert an element into the pocket that forms the internal baffles. The outside shape of the earplug is shown having flanges, but other outside shapes can be used.

Thus, the invention provides an earplug of the type that has a pocket, which can be constructed at low cost and that increases sound attenuation. The pocket is formed by a core pin that is removed from the earplug after it is molded as by injection molding to leave a pocket. The earplug includes a shell of elastomeric material that includes a sleeve that surrounds the pocket and that forms a plurality of baffles that each extends partially across the pocket. The baffles each preferably extends across at least about half of the diameter of the pocket and blocks an average of at least half of the cross-section of the pocket at the location of the baffle as seen along the axis of the earplug. The baffles are staggered, with adjacent baffles extending into the pocket from opposite sides of the pocket. The rear pocket portion is closed by a blocker means that either completely seals the pocket or that leaves a pin hole to allow the outflow of air from the pocket and the later inflow of air.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug having a body of elastomeric material, said body having an axis extending in front and rear directions and said body having a body front portion with an outer surface that is shaped for insertion into a person's ear canal to seal against ear canal walls and having a body rear portion that extends rearward of said body front portion, wherein:

said body has a pocket that has pocket front and side walls that enclose a front and sides of said pocket, said pocket having a rear end that is blocked against the free passage of sound forwardly into said pocket;

said body having a pocket front portion with a plurality of axially spaced internal baffles that each extends across a majority of the cross-sectional area of the pocket when the earplug is not compressed, with the baffles being free of connection to each other except through said pocket side walls.

2. The earplug described in claim 1 wherein:

said pocket front portion has primarily circular cross-sections as seen in sectional views taken perpendicular to said axis, and each baffle has a free edge that is spaced from walls of said pocket, the free edge leaving a primarily circular pocket internal surface opposite the free edge.

3. The earplug described in claim 1 wherein:

each of said baffles extends laterally from one side of said pocket walls towards an opposite side of the pocket, and each of said baffles has a free edge (77) spaced from a laterally opposite side (76) of the pocket when the earplug front portion does not lie in an ear canal;

when said body front portion lies compressed in a human ear canal, the free edge of at least one baffle lies in automatically releasable contact with a laterally opposite side (76) of the pocket so the baffle automatically moves away from such laterally opposite side when the earplug is removed from the ear.

4. An earplug having a body of elastomeric material, said body having an axis extending in front and rear directions and said body having a body front portion with an outer surface that is shaped for insertion into a person's ear canal to seal against ear canal walls, wherein:

said body has a pocket with front and side walls that enclose a front and sides of said pocket, said pocket having a rear end that is blocked against the free passage of sound forwardly into said pocket, said pocket having a front portion with inside walls of primarily cylindrical shape to have approximately circular cross-sections with said circular cross-sections each having a diameter D;

said body front portion having a plurality of internal baffles that each extends laterally across a majority of the cross-section of the pocket, with each baffle having a free edge that, as seen in a view along said axis, is spaced from a front pocket side wall when the earplug is not compressed, with the free edge having a length that is a majority of said diameter D.

5. The earplug described in claim 4 wherein:

said baffles include first and second baffles are spaced apart along said axis and unconnected to each other except through said pocket side walls, said baffles having blocking portions lying on opposite sides of said axis;

said body and said baffles are integrally molded with each other, with said baffle free edges spaced from said pocket side walls so a single core pin that has slots that form an internal surface of said pocket and said baffles within a mold, can be removed from the earplug.

6. The earplug described in claim 4 wherein:

the free edges (77) of said baffles are each spaced from a laterally opposite side (76) of the pocket when the earplug front portion does not lie in a ear canal;

said free edges being free to deflect toward opposite sides of said pockets, so when said body front portion lies in a human ear canal, the free edge of at least one baffle lies in releasable contact with a laterally opposite side (76) of the pocket so the baffle automatically moves away from said opposite side when the earplug is removed from the ear.

7. An earplug having a body of elastomeric material, said body having an axis extending in front and rear directions and said body having a body front portion with an outer surface that is shaped for insertion into a person's ear canal to seal against ear canal walls, wherein:

said body has walls forming a pocket with pocket front and side walls that enclose a front and sides of said pocket, said pocket having a rear end that is blocked against the free passage of sound forwardly into said pocket, and said pocket having a pocket front portion;

said body front portion having a plurality of baffle means spaced along said axis, each extending from a first side of said pocket across a majority of said pocket front portion towards an opposite second side of the pocket portion, and each baffle means having a baffle means free edge spaced from said opposite second side of the pocket when said body front portion is not compressed, for blocking the passage of sound along said pocket in the direction of said axis and for allowing the body to be compressed until a free edge of at least one of the flange means abuts the opposite side of the pocket.

8. The earplug described in claim 7 wherein:

said baffle means are formed integrally with and of the same elastomeric material as said body.

\* \* \* \* \*